United States Patent
Chen et al.

(10) Patent No.: US 12,216,233 B2
(45) Date of Patent: Feb. 4, 2025

(54) SYSTEMS AND METHODS FOR ULTRASOUND ATTENUATION COEFFICIENT ESTIMATION

(71) Applicant: Mayo Foundation for Medical Education and Research, Rochester, MN (US)

(72) Inventors: Shigao Chen, Rochester, MN (US); Ping Gong, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 17/627,531

(22) PCT Filed: Jul. 20, 2020

(86) PCT No.: PCT/US2020/042733
§ 371 (c)(1),
(2) Date: Jan. 14, 2022

(87) PCT Pub. No.: WO2021/016164
PCT Pub. Date: Jan. 28, 2021

(65) Prior Publication Data
US 2022/0283278 A1    Sep. 8, 2022

Related U.S. Application Data

(60) Provisional application No. 62/876,253, filed on Jul. 19, 2019.

(51) Int. Cl.
G01S 7/52    (2006.01)
A61B 8/00    (2006.01)

(52) U.S. Cl.
CPC ............ *G01S 7/52036* (2013.01); *A61B 8/00* (2013.01); *G01S 7/52057* (2013.01)

(58) Field of Classification Search
CPC .... G01S 7/52036; G01S 7/52057; A61B 8/00
See application file for complete search history.

(56) References Cited

U.S. PATENT DOCUMENTS 4,414,850 A    11/1983    Miwa
5,097,836 A    3/1992    Cohen
(Continued)

FOREIGN PATENT DOCUMENTS

WO    2017146886 A1    8/2017
WO    2018237244 A1    12/2018

OTHER PUBLICATIONS

Ping et al.; "System-Independent Ultrasound Attenuation Coefficient Estimation Using Spectra Normalization"; Ultrasonics, Ferroelectrics, and Frequency Control; vol. 66, No. 5; pp. 867-875 (Year: 2019).*

(Continued)

*Primary Examiner* — Dixomara Vargas
(74) *Attorney, Agent, or Firm* — Quarles & Brady LLP

(57) ABSTRACT

Ultrasound attenuation coefficient estimation ("ACE") techniques that can ameliorate frequency power ratio curve oscillations caused by signal interferences, non-uniform tissue structures, or both, are described. The resulting smoothed frequency power ratio curves enable more accurate ACE and reduced region-of-interest ("ROI") sizes for linear regression.

14 Claims, 12 Drawing Sheets

(56) References Cited

U.S. PATENT DOCUMENTS

| | | | |
|---|---|---|---|
| 6,743,174 | B2 | 6/2004 | Ng et al. |
| 8,679,019 | B2 | 3/2014 | Jurvelin et al. |
| 11,166,699 | B2 | 11/2021 | Labyed et al. |
| 2007/0106157 | A1* | 5/2007 | Kaczkowski ......... A61B 8/587 600/438 |
| 2009/0143681 | A1 | 6/2009 | Jurvelin |
| 2010/0036292 | A1* | 2/2010 | Darlington ............... A61N 7/00 601/2 |
| 2010/0249590 | A1 | 9/2010 | Kanayama et al. |
| 2012/0163691 | A1 | 6/2012 | Walker et al. |
| 2013/0035594 | A1 | 2/2013 | Eda |
| 2014/0114189 | A1 | 4/2014 | Kanayama |
| 2014/0109675 | A1 | 5/2014 | Langlois et al. |
| 2017/0258453 | A1 | 9/2017 | Takayama |
| 2017/0273667 | A1 | 9/2017 | Labyed |
| 2018/0220997 | A1 | 8/2018 | Song |
| 2020/0146656 | A1* | 5/2020 | Gong .................... G01S 15/892 |

OTHER PUBLICATIONS

Lauren et al.; "Techniques and Evaluation from a Cross-Platform Imaging Comparison of Quantitative Ultrasound Parameters in Vivo Rodent Fibroadenoma Model"; Ultrasonics, Ferroelectrics, and Frequency Control; vol. 60, No. 7; pp. 1386-1400 (Year: 2013).*

Duck F.A., "Chapter 4—Acoustic Properties of Tissue at Ultrasonic Frequencies," in Physical Properties of Tissues, London: Academic Press, 1990, pp. 73-135.

Golub G. et al., "The Differentiation of Pseudo-Inverses and Nonlinear Least Squares Problems Whose Variables Separate," SIAM Journal on Numerical Analysis, vol. 10, No. 2, pp. 413-432, Apr. 1, 1973 1973.

Gong, P. et al., "System-Independent Ultrasound Attenuation Coefficient Estimation Using Spectra Normalization", IEEE Transactions on Ultrasonics, Ferroelectrics and Frequency Control, IEEE, vol. 66, No. 5, Mar. 5, 2019, pp. 867-875.

Kim H. et al., "Hybrid Spectral Domain Method for Attenuation Slope Estimation," Ultrasound in Medicine and Biology, vol. 34, No. 11, pp. 1808-1819, Nov. 2008.

Kuc R. et al., "Reduced-order Autoregressive Modeling for Center-frequency Estimation," Ultrasonic Imaging, vol. 7, No. 3, pp. 244-251, Jul. 1985.

Labyed, Y, et al. "A theoretical comparison of attenuation measurement techniques from backscattered ultrasound echoes." The Journal of the Acoustical Society of America 129.4 (2011): 2316-2324.

Labyed, Y. et al. "Estimating the total ultrasound attenuation along the propagation path by using a reference phantom." The Journal of the Acoustical Society of America 128.5 (2010): 3232-3238.

Lin, T. et al., "Correlation of Ultrasonic-Attenuation with Pathologic Fat and Fibrosis in Liver-disease," Ultrasonic Imaging, vol. 10, No. 1, pp. 59-59, Jan. 1988.

Lu, Z.F. et al., "Ultrasound backscatter and attenuation in human liver with diffuse disease," Ultrasound in Medicine and Biology, vol. 25, No. 7, pp. 1047-1054, Sep. 1999.

Nam, K. et al., "Simultaneous Backscatter and Attenuation Estimation using a Least Squares Method with Constraints," Ultrasound in Medicine and Biology, vol. 37, No. 12, pp. 2096-2104, Dec. 2011.

Oelze M.L. et al., "Review of Quantitative Ultrasound: Envelope Statistics and Backscatter Coefficient Imaging and Contributions to Diagnostic Ultrasound," IEEE Transactions on Ultrasonics Ferroelectrics and Frequency Control, vol. 63, No. 2, pp. 336-351, Feb. 2016.

Sasso, M. et al., "Controlled Attenuation Parameter (CAP): A Novel VCTE (TM) Guided Ultrasonic Attenuation Measurement for the Evaluation of Hepatic Steatosis: Preliminary Study and Validation in a Cohort of Patients with Chronic Liver Disease from Various Causes," Ultrasound in Medicine and Biology, vol. 36, No. 11, pp. 1825-1835, Nov. 2010.

Taylor, Kjw et al., "Quantitative US Attenuation in Normal Liver and in Patients with Diffuse Liver-Disease—Importance of Fat," Radiology, vol. 160, No. 1, pp. 65-71, Jul. 1986.

Yao, L.X. et al., "Backscatter Coefficient Measurements Using a Reference Phantom to Extract Depth-Dependent Instrumentation Factors," Ultrasonic Imaging, vol. 12, No. 1, pp. 58-70, Jan. 1, 1990 1990.

Lizzi, F. L. et al., "Tissue Signature Characterization Utilizing Frequency Domain Analysis," 1976 Ultrasonics Symposium, pp. 714-719, 1976 (Year: 1976).

O'Donnell, M., "Effects of Diffraction on Measurements of the Frequency-Dependent Ultrasonic Attenuation," IEEE Transactions on Biomedical Engineering, vol. BME-30, No. 6, pp. 320-326, Jun. 1983 (Year: 1983).

Parker, K. J. et al., "Measurement of Ultrasonic Attenuation Within Regions Selected from B-Scan Images," IEEE Transactions on Biomedical Engineering, vol. BME-30, No. 8, pp. 431-437, Aug. 1983 (Year: 1983).

Kim, H. et al., "Estimation of Ultrasound Attenuation from Broadband Echo-Signals Using Bandpass Filtering," IEEE Transactions on Ultrasonics, Ferroelectrics, and Frequency Control, vol. 55, No. 5, pp. 1153-1159, May 2008 (Year: 2008).

Hasan et al., "Using Nearest Neighbors for Accurate Estimation of Ultrasonic Attenuation in the Spectral Domain," IEEE Transactions on Ultrasonics, Ferroelectrics, and Frequency Control, vol. 60, No. 6, pp. 1098-1114, Jun. 2013 (Year: 2013).

Kanayama, Y. et al., "Real-Time Ultrasound Attenuation Imaging of Diffuse Fatty Liver Disease", Ultrasound in Medicine and Biology , vol. 39, No. 4, pp. 692-705, Apr. 2013 (Year: 2013).

Mo, T. et al., "Calculations of Radar Backscattering Coefficient of Vegetation-Covered Soils," Remote Sensing of Environment, vol. 15, pp. 119-133, 1984 (Year: 1984).

Boote, E. J. et al., "Instrument-Independent Acoustic Backscatter Coefficient Imaging," Ultrasonic Imaging, vol. 10, pp. 121-138, 1988 (Year: 1988).

Wear, K. A. et al., "Measurements of ultrasonic backscatter Coefficients in human liver and kidney in vivo," Journal of the Acoustical Society of America, vol. 98, No. 4, pp. 1852-1857, Oct. 1995 (Year: 1995).

Lavarello, R. J. et al., "On the estimation of backscatter coefficients using single-element focused transducers," Journal of the Acoustical Society of America, vol. 129, No. 5, pp. 2903-2911, May 2011 (Year: 2011).

Cook, J.R. et al., "Tissue-mimicking phantoms for photoacoustic and ultrasonic imaging," Optical Society of America, vol. 2, No. 11, pp. 3193-3206 Oct. 2011 (Year: 2011).

Nam, K. et al., "Ultrasonic Attenuation and Backscatter Coefficient Estimates of Rodent-Tumor-Mimicking Structures: Comparison of Results among Clinical Scanners," Ultrasonic Imaging, vol. 33, No. 4, pp. 233-250, Oct. 2011 (Year: 2011).

O'Leary, D.P. et al., "Variable projection for nonlinear least squares problems," Computational Optimization and Applications, vol. 54, pp. 579-593, Apr. 2013 (Year: 2013).

Evans, J.D. et al., "Prospects for in vivo estimation of photon linear attenuation coefficients using postprocessing dual-energy CT imaging on a commercial scanner," Medical Physics, vol. 40, No. 12, pp. 121914-1-121914-16, Dec. 2013 (Year: 2013).

Samimi, K. et al., "Lower Bound on Estimation Variance of the Ultrasonic Attenuation Coefficient Using the Spectral-Difference Reference-phantom Method," Ultrasonic Imaging, vol. 39, No. 3, pp. 151-171, Oct. 2016 (Year: 2016).

Omari, E. A., et al. "Signal to noise ratio comparisons for ultrasound attenuation slope estimation algorithms." Medical physics 41.3 (2014): 032902.

* cited by examiner

Frequency Power Curves
as a Function of Depth

Frequency Power Ratio Curve
with Linear Regression

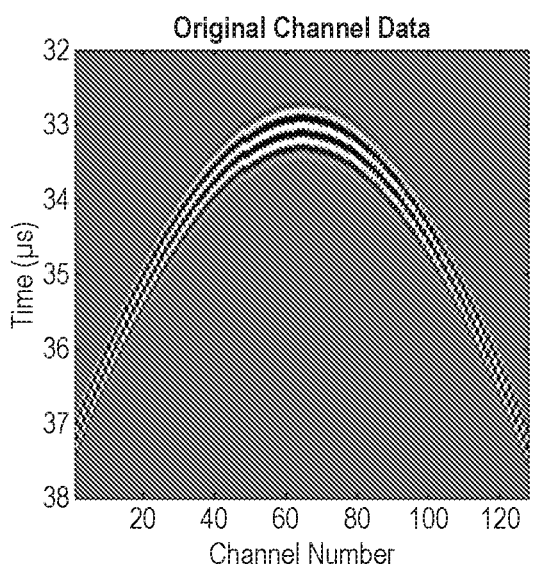
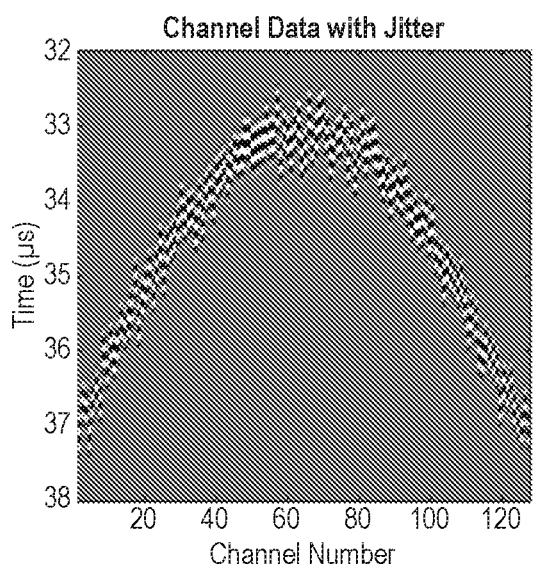
FIG. 3A    FIG. 3B
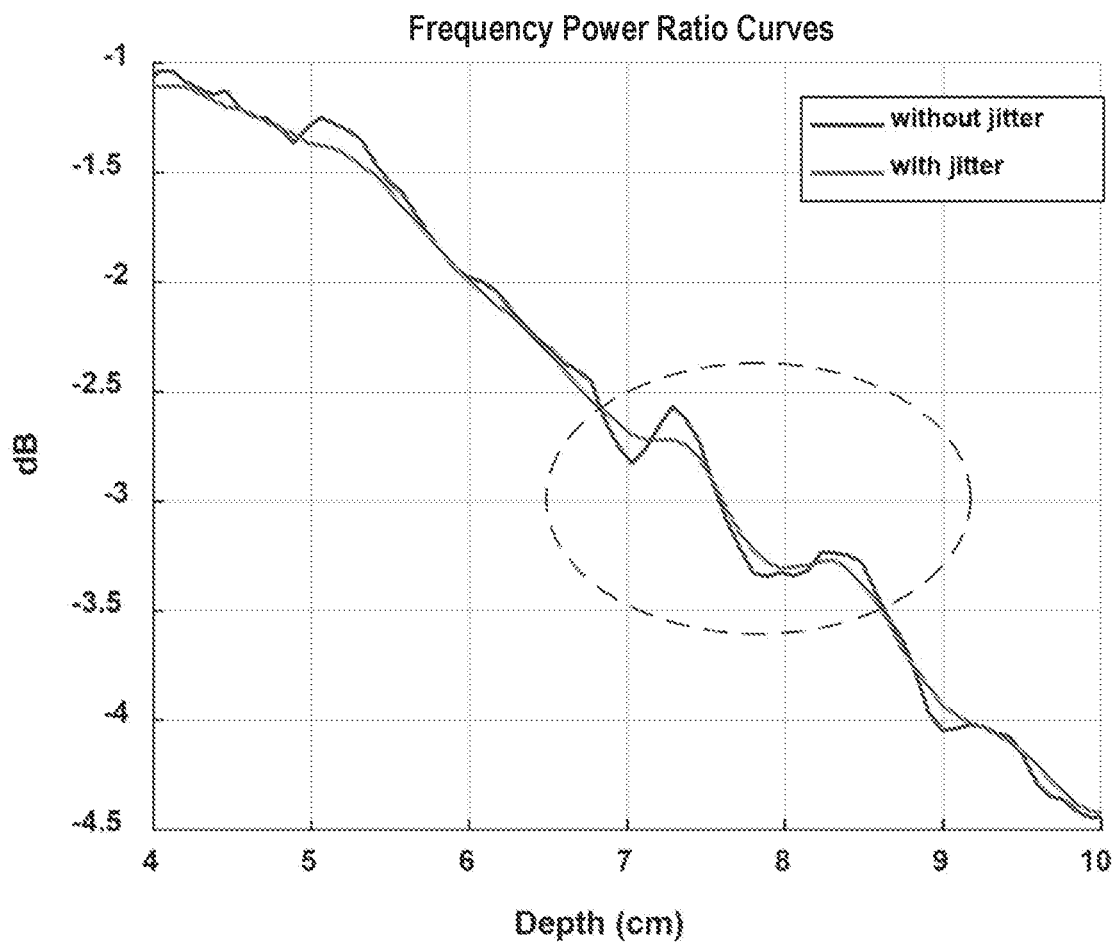
FIG. 4

SYSTEMS AND METHODS FOR ULTRASOUND ATTENUATION COEFFICIENT ESTIMATION

CROSS-REFERENCE TO RELATED APPLICATIONS

This application represents the national stage entry of PCT/US2020/042733 filed on Jul. 20, 2020 and claims the benefit of U.S. Provisional Patent Application Ser. No. 62/876,253, filed on Jul. 19, 2019, and entitled "SYSTEMS AND METHODS FOR ULTRASOUND ATTENUATION COEFFICIENT ESTIMATION," the contents of which is herein incorporated by reference in its entirety.

BACKGROUND

Ultrasound attenuation coefficient estimation ("ACE") has potential for many clinical applications, including differentiating tumors and quantifying fat content in the liver. For instance, in the non-limiting example of fat content detection, the accumulation of fatty droplets in the liver can lead to steatosis, and in many cases, steatosis might progress to fibrosis, cirrhosis, liver failure, or hepatocellular carcinoma. Fat content can increase ultrasound attenuation during ultrasound propagation in the liver; therefore, the ultrasound attention coefficient can be a useful parameter to quantify liver fat. Compared with the gold standard, liver biopsy, ACE provides non-invasive and repeatable measurements, which is important for both initial screening and follow-up exams. Hence, accurate ACE has clinical utility in fatty liver detection and assessment, among other clinical applications.

SUMMARY OF THE DISCLOSURE

The present disclosure addresses the aforementioned drawbacks by providing a method for estimating ultrasound attenuation coefficient data using an ultrasound system. Ultrasound data acquired from a subject with an ultrasound system are accessed with a computer system. The ultrasound data contain subsets of ultrasound data acquired with different characteristics. Averaged ultrasound data are generated with the computer system by averaging the ultrasound data corresponding to the subsets of ultrasound data. Frequency power ratio curve data are generated from the averaged ultrasound data using the computer system, wherein the frequency power ratio curve data have reduced frequency power ratio curve oscillations. Attenuation coefficient data are generated from the frequency power ratio curve data using the computer system.

It is another aspect of the present disclosure to provide a method for estimating ultrasound attenuation coefficient data using an ultrasound system. Ultrasound data acquired from a subject with an ultrasound system are accessed with a computer system. Non-uniform structures are detected in the ultrasound data using the computer system. Frequency power ratio curve data are generated from the ultrasound data using the computer system while processing the ultrasound data to reduce contributions from ultrasound data corresponding to the detected non-uniform structures. The frequency power ratio curve data have reduced frequency power ratio curve oscillations. Attenuation coefficient data are generated from the frequency power ratio curve data using the computer system.

It is still another aspect of the present disclosure to provide a method for estimating ultrasound attenuation coefficient data using an ultrasound system. Ultrasound data acquired from a subject with an ultrasound system are accessed with a computer system. A region-of-interest ("ROI") is selected in the ultrasound data using the computer system, and the ROI is divided into a plurality of subregions. Frequency power ratio curve data are generated for each of the plurality of subregions from the ultrasound data corresponding to each respective subregion. Attenuation coefficient data are generated for each of the plurality of subregions from the frequency power ratio curve data corresponding to each respective subregion, wherein the attenuation coefficient data are generated based on a linear fitting. Final attenuation coefficient data are generated for the ROI from the attenuation coefficient data for each of the plurality of subregions using a linearity metric of each linear fitting a quality control for generating the final attenuation coefficient data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 3A shows an example of unaltered channel data acquired with an ultrasound system.

FIG. 3B shows an example of the channel data of FIG. 3A to which random jitters have been added.

FIG. 4 shows an example of frequency power ratio curves generated from ultrasound data with (red) and without (blue) jitter added.

DETAILED DESCRIPTION

Described here are systems and methods for improved ultrasound attenuation coefficient estimation ("ACE") techniques. In general, the systems and methods described in the present disclosure can ameliorate frequency power ratio curve oscillations that are caused by signal interferences, non-uniform tissue structures, or both. The resulting smoothed frequency power ratio curves enable more accurate ACE and reduced region-of-interest ("ROI") sizes for linear regression.

In ultrasound imaging, the power spectrum of backscattered RF signals can be modeled as, $$S(f_i, z_k) = G(f_i) \cdot TGC(z_k) \cdot D(f_i, z_k) \cdot BSC(f_i) \cdot A(f_i, z_k) \quad (1);$$

where $G(f_i)$ accounts for the transmit and receive transducer responses at the frequency $f_i$, where i is the frequency component index); $TGC(z_k)$ is the time-gain compensation ("TGC"), varying as a function of depth, $z_k$, where k is the depth index); $D(f_i, z_k)$ is the combined effects of focusing, beamforming, and diffraction; $BSC(f_i)$ is the backscatter coefficient which is assumed be to uniform in the region-of-interest ("ROI"); and $A(f_i, z_k)$ is the frequency dependent attenuation, which can be expressed as, $$A(f_i, z_k) = e^{-4\alpha f_i z_k} \quad (2);$$

where $\alpha$ is the attenuation coefficient. In many instances, it can be assumed that $A(f_i, z_k)$ is uniform in the ROI and that it is has a linear frequency dependency. The shape of the ROI is flexible, and in some instances may be a rectangle, a square, a sector, and so on. This type of model can be generally applicable to all ultrasound systems regardless of the beam pattern (e.g., unfocused or focused).

The ultrasound attenuation coefficient can be measured from the decay of ultrasound echo signal over known propagation distance. FIGS. 1A-1D show an example process for implementing ACE using a reference frequency method, such as those described in co-pending U.S. Patent Application Publication No. US2020/0146656, which is herein incorporated by reference in its entirety.

Figure 1A:
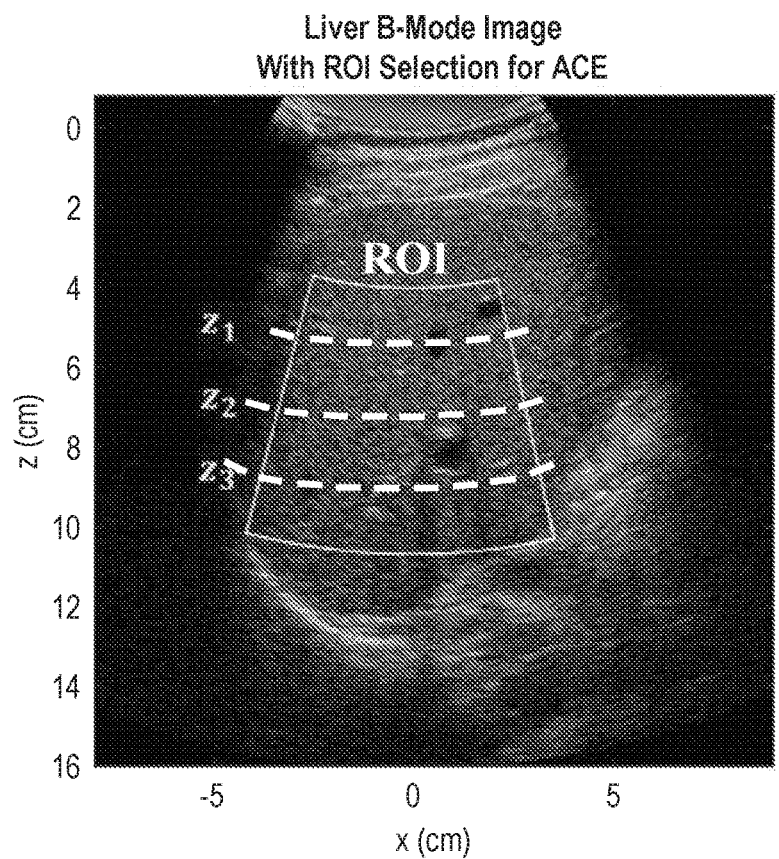
FIG. 1A shows an example of a liver B-mode image with a selected region-of-interest ("ROI") and multiple depth locations selected for attenuation coefficient estimation ("ACE").
Figure 1B:
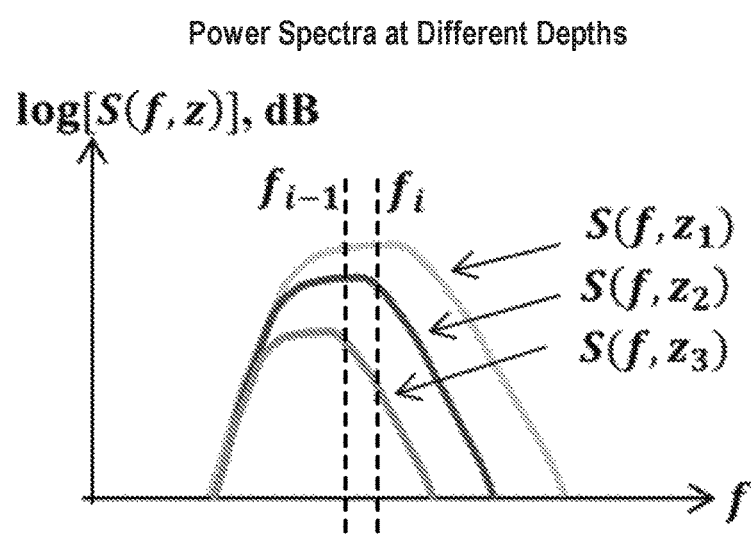
FIG. 1B shows an example of power spectra at the depth locations indicated in FIG. 1A.
Figure 1C:
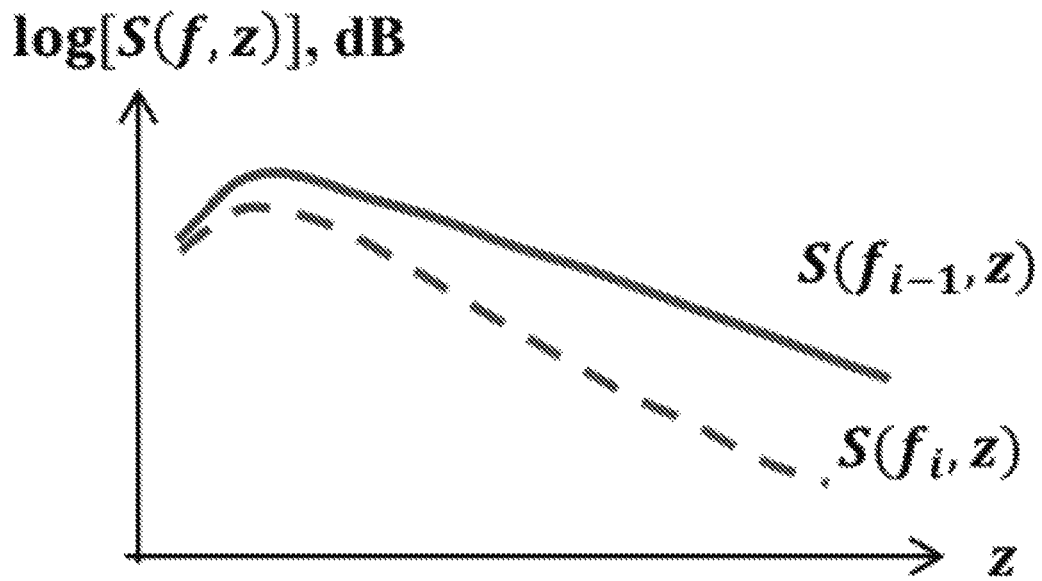
FIG. 1C shows an example of frequency power curves as a function of depth.

An ROI is first selected from an ultrasound B-mode image, as shown in FIG. 1A. Then, the selected ROI is divided into small data blocks along the axial direction (with or without overlap). As shown in FIG. 1B, the power spectra of all of the A-line segments in the given data block are calculated and then averaged laterally to obtain the mean power spectra (i.e., S(f,z)) at a specific depth (e.g. $z_1$, $z_2$, or $z_3$). FIG. 1C shows the frequency power curves as a function of depth at two frequency components, $f_i$ and $f_{i-1}$. Due to ultrasound attenuation, the logarithm of frequency power should change linearly with depth; however, this linear trend can be confounded by system effects, such as focusing and time gain compensation ("TGC").

Figure 1D:
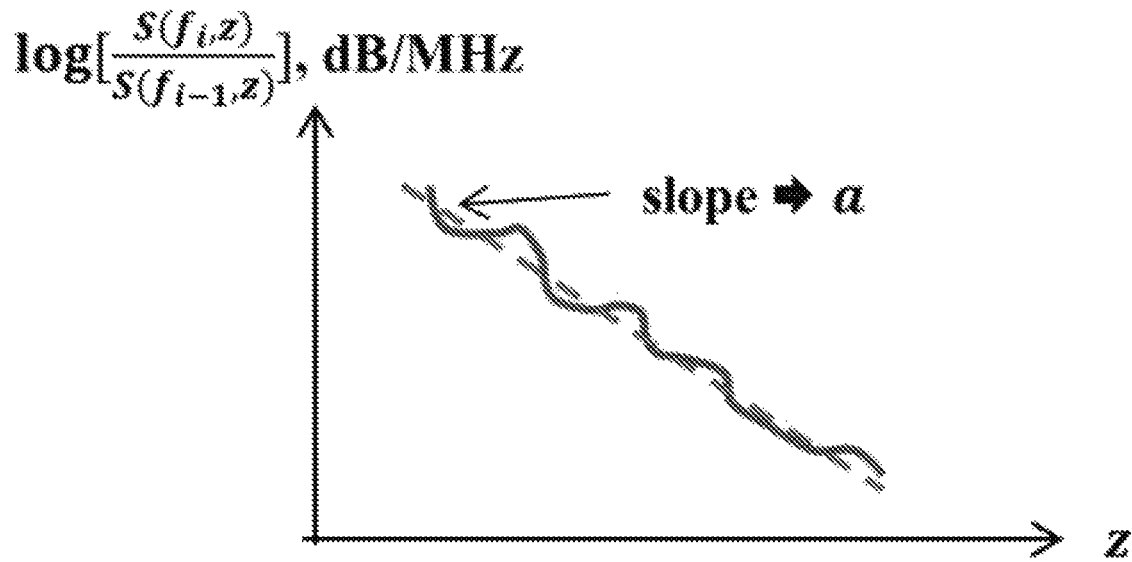
FIG. 1D shows an example of a frequency power ratio curve and a corresponding linear regression.

The reference frequency method cancels the system dependent effects by calculating the frequency power ratio between two different frequency components. In another ACE method, the reference phantom method, the frequency power ratio is calculated between the testing target and a well-calibrated reference phantom to normalize all the system effects. After system effects normalization, there is a generally linear relationship between frequency power ratio in the logarithm domain and imaging depth, as shown in FIG. 1D. A linear regression can be applied to the frequency power ratio curve to estimate the attenuation coefficient. The final estimation can be displayed as a single value or as a two-dimensional attenuation coefficient map, which may be overlaid on the selected ROI.

The frequency power ratio curves usually contain oscillations that undermine the linear regression, and therefore the accuracy of ACE. These oscillations can be caused by small non-uniform structures in the tissue; spatial variations due to constructive and destructive interferences from the backscattered signals; and noise. Methods for reducing noise bias that contaminates the signals for ACE, such as those described in co-pending Patent Application No. PCT/US2020/012325, which is herein incorporated by reference in its entirety, can be used to address oscillations caused by noise.

It is an aspect of the present disclosure to provide systems and methods for further improving the robustness of ACE, such that the accuracy of different ACE methods (e.g., reference phantom method, reference frequency method) can be significantly increased.

In one aspect, the systems and methods described in the present disclosure provide for improved ACE by implementing a quality control factor to stabilize ACE performance. The quality control factor can be based on the linearity of frequency power ratio curves, such as the linearity of frequency power ratio curves in sub-ROIs.

Figure 2:
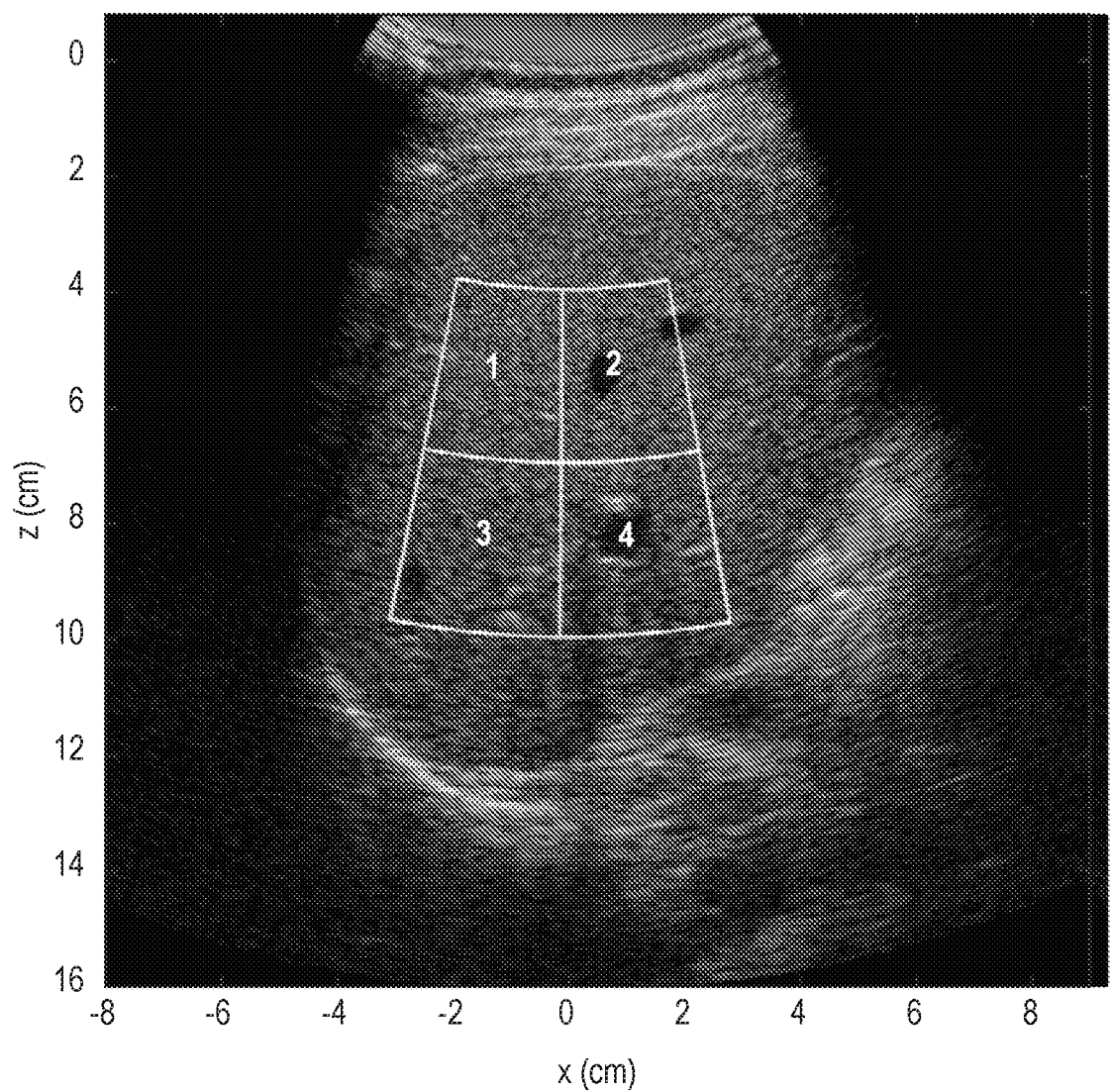
FIG. 2 shows an example of an ROI divided into multiple non-overlapping subregions, or sub-ROIs.

As one non-limiting example, the coefficient of determination ($R^2$ or adjusted $R^2$) can be used as an indicator of the goodness of linear regression. The selected ROI used for ACE can be divided into subregions (i.e., sub-ROIs), with or without overlapping. FIG. 2 shows an example where an ROI is divided into four non-overlapping sub-ROIs (i.e., sub-ROIs 1-4). ACE can be performed on each sub-ROI. In some instances, the estimated attenuation value can then be displayed as a single value assigned to the center pixels of the selected sub-ROI or a two-dimensional ACE map overlaid on all pixels within selected sub-ROI. The ACE calculation can be repeated for the next overlapping (or non-overlapping) sub-ROI until all sub-ROIs undergo the same ACE process. For an image pixel that is assigned attenuation values by multiple different sub-ROIs, the final estimate for that pixel can be calculated as the average of all attenuation values from different sub-ROIs. The final attenuation value of the entire ROI can then be selected as the average from all pixels with estimated attenuation values.

Additionally or alternatively, ACE can be performed inside each sub-ROI with $R^2$ determined. The final attenuation value of the entire ROI can then be selected as the attenuation value obtained from the sub-ROI with maximum $R^2$ (i.e., $R_{max}^2$). The attenuation assigned to the ROI can also be selected as the median value of attenuation estimations from all sub-ROIs, the mean value of attenuation estimations from all sub-ROIs, and so on.

Moreover, an $R^2$ threshold can be applied to exclude the ACE estimations with $R^2$ values smaller than a predefined limit before calculating the median or mean. Such an $R^2$ threshold can be selected as a specific number (e.g., $R^2>0.90$) or can be adaptively determined regarding the maximum $R^2$ obtained (e.g. $R^2>0.90\times R_{max}^2$). The $R^2$ values corresponding to each sub-ROI can also be used as weighting factors when calculating the mean attenuation values from sub-ROIs.

Note that in the example of FIG. 2, $R^2$ was used as a linearity indicator. The disclosed methods should also apply to other linearity-related coefficients. In still other implementations, a nonlinear regression can be used to estimate the attenuation coefficient data. In these instances, nonlinearity-related coefficients can be used as the quality control metric.

In one aspect, the systems and methods described in the present disclosure provide for improved ACE by reducing oscillations in frequency power ratio curves by changing signal interference patterns in a way that reduces these oscillations. One reason for the oscillations on the frequency power ratio curves is the spatial variations due to constructive and destructive interferences from the backscattered signals from many tissue scatterers. Adding ultrasound jitters can change these signal interference patterns, and, thus, can be used to reduce the oscillations on the frequency power ratio curves.

Ultrasound jitters can be generated in a number of different ways. As one example, different ultrasound jitters can be assigned to different transmitting elements. As another example, different ultrasound jitters can be assigned to different receiving channels. Additionally or alternatively, different ultrasound jitters can be assigned to both transmitting elements and receiving channels. In some instances, the ultrasound jitters can be applied to all of the available channels, and in other instances can be applied to only a subset of the available channels.

As one example, the received channel data are shifted with ultrasound jitters before beamforming. FIG. 3A shows an example of original channel RF data received from a point target located at the imaging center. The ultrasound signal arrival time in different channels is shown as a smooth curve in FIG. 3A, depending on the ultrasound travel distance from the target to the receive channel. However, when random jitter is added by shifting the received channel data, the smooth curve becomes zigzag-shaped, as shown in FIG. 3B.

The amount of jitters can be randomly determined or specifically designed. Then, beamforming can be applied, followed with ACE analysis steps. The process of assigning jitters can be repeated for multiple times for the same set of received channel data. The power spectra of beamformed A-lines with different jitters can be averaged to reduce the oscillations on the frequency power ratio curves more effectively.

FIG. 4 shows one non-limiting example of frequency power ratio curves with and without jitter added to the channel data. In this example, random jitters were assigned to the same set of channel data for 20 times and the results were averaged. The oscillations on the frequency power ratio curve were significantly decreased (as shown in the blacked dashed ellipse).

In one aspect, the systems and methods described in the present disclosure provide for improved ACE by reducing oscillations in frequency power ratio curves by averaging multiple power spectra obtained from different A-lines. In general, multiple power spectra can be averaged with an assumption that the testing medium (e.g., the tissue being imaged) is homogenous. Advantageously, uncorrelated A-lines can be used for effective averaging. In this way, multiple B-mode frames can be acquired with the subject breathing freely during real-time in-vivo scanning. As another example, the sonographer can slightly move the probe during image acquisition to obtain data from different regions of the target tissue.

Figure 5:
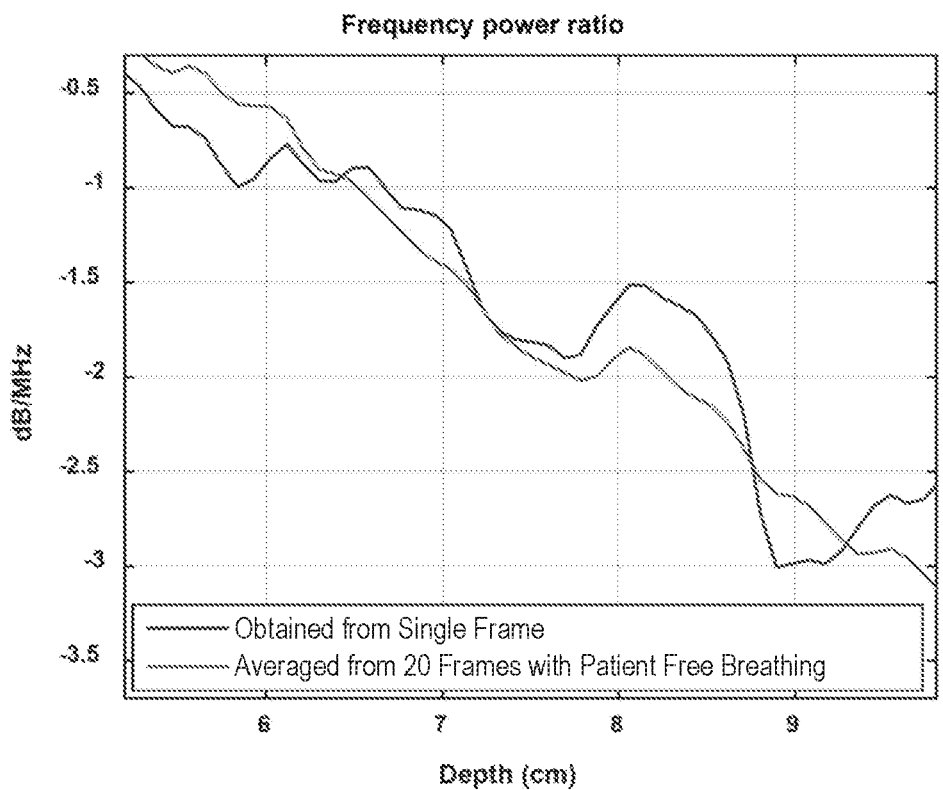
FIG. 5 shows an example of frequency power ratio curves based on a single data frame (blue) and an average of twenty data frames acquired while a subject was freely breathing (red).

The respiration-induced tissue motion or probe-moving-induced motion can reduce the correlation among A-lines in different ultrasound data frames. The spectra of these A-lines can then be averaged to smooth the frequency power ratio curves for ACE. FIG. 5 shows an example of the frequency power ratio curves obtained from a single data frame, in comparison with the result averaged from 20 frames of real-time acquisition when the subject was breathing freely. The oscillations on the averaged frequency power ratio curve from multiple frames are significantly reduced.

Figure 6:
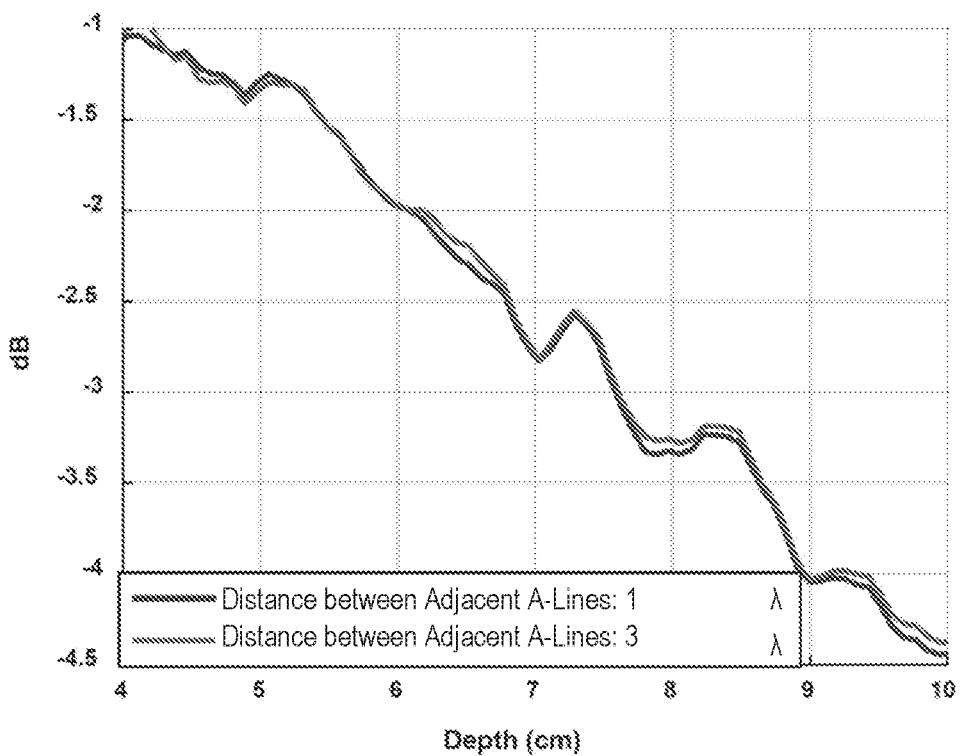
FIG. 6 shows an example of frequency power ratio curves generated from ultrasound data acquired with different spacing between adjacent A-lines.

To include more uncorrelated A-lines for spectra averaging, more B-mode frames can be used. Thus, a higher frame rate may be advantageous. For focused beam imaging, the line density in one B-mode frame can be decreased to increase the frame rate. For example, every other A-line or every other two A-lines can be acquired. FIG. 6 shows one non-limiting example of frequency power ratio curves acquired with different line densities. The red curve was acquired with only one-third of the A-lines used for blue curve, but retained similar performance.

Thus, in some instances, sparsely-sampled A-line acquisitions can be used to enhance the frame rate with comparable performance as compared to densely-sampled A-line acquisitions. The increased frame rate offers more frames available for ACE processing. When motion is involved among frames (e.g., patient respiration or probe moving as described above), these additional B-mode images obtained by reducing the line density can provide more uncorrelated frames and thus more uncorrelated A-lines for averaging. If the imaged target is relatively stationary (i.e., the A-lines have high correlation among different frames), these additional frames still offers benefits for ACE. For instance, the A-lines in different frames can be averaged in the time domain to improve the signal-to-noise ratio ("SNR").

Additionally or alternatively, the correlations of A-lines among different frames can be decreased by using different transmission sequences to acquire these additional frames. For example, transmission sequences using plane/diverging waves, focused beams at different focusing depths, or steered focused beams (i.e., crossbeam), can be used as the different transmission sequences.

Figure 7:
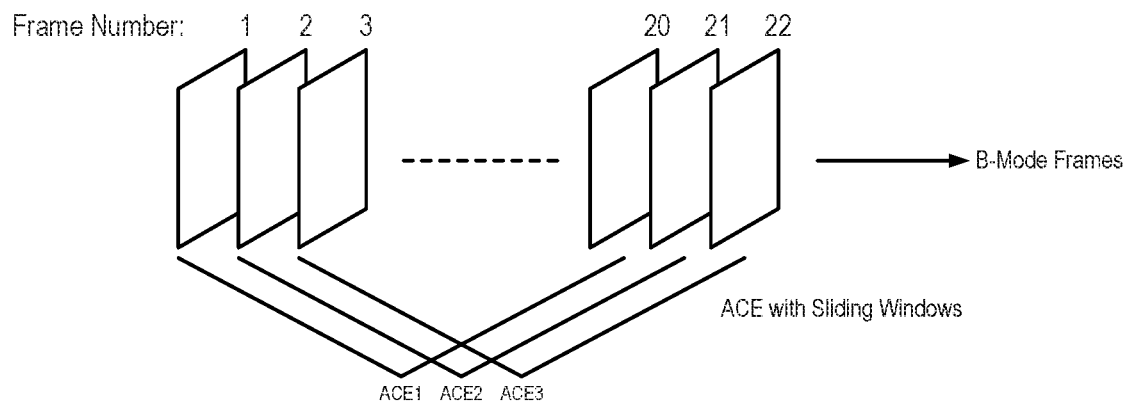
FIG. 7 shows an example of ACE processing using a sliding window.

The high frame rate of sparsely-sampled A-line acquisitions can also benefit real-time ACE applications. Other methods can also be applied to facilitate real-time ACE. For example, a sliding window can be used, as shown in FIG. 7. In these instances, ACE is performed on every 20 consecutive B-mode frames: ACE1 uses frames 1-20; ACE2 uses frames 2-21, and so on. The implementation of a sliding window enables the same frame rate for attenuation estimation as for ultrasound B-mode image acquisitions.

In one aspect, the systems and methods described in the present disclosure provide for improved ACE by using transmission with different pulse designs.

Most ACE methods usually assume that the tissue properties inside the selected ROI are uniform. However, in practice, tissues typically contain complicated structures that violate the uniformity assumption. One non-limiting example is the vessels inside the liver parenchyma, which usually present as dark structures in B-mode image as compared to surrounding tissues. These non-uniform structures are another factor causing the oscillations on the frequency power ratio curves.

Transmissions with longer pulses usually lead to poor image axial resolution. This may change the signal interference pattern and blur the non-uniform tissue structures, which may reduce the oscillations on the frequency power ratio curves. In addition, the spectra of A-lines acquired with different pulse designs (e.g., different pulse lengths: $\lambda_1$, $\lambda_2$, $\lambda_3$; chirp pulses; different pulse coding, such as for Golay coded pulses) can be averaged to further reduce the oscillations.

In one aspect, the systems and methods described in the present disclosure provide for improved ACE by detecting and removing non-uniform structures from a selected ROI before ACE analysis is implemented. To rule out the non-uniform structures inside the selected ROI before ACE analysis, upper and lower image intensity thresholds can be determined. Other vessel detection or edge detection techniques can also be applied to identify non-uniform structures in the ultrasound data. The upper and lower intensity thresholds can be determined in a number of different ways.

As one example, the upper and lower intensity thresholds can be defined globally by regarding the statistics of the intensity values (e.g., maximum, minimum, median, mean) of the entire image, or the entire ROI. In this example, an ROI was selected from a B-mode image. For one non-limiting example, the lower threshold can be selected as 35 dB below the maximum intensity of the ROI; however, other threshold values can also be implemented. Image intensities smaller than the lower threshold can be assumed as non-uniform tissue structures, such as vessels or shadow effects. For another non-limiting example, the upper threshold can be selected as 10 dB below the maximum intensity of the ROI; however, other threshold values can also be implemented. Image intensities larger than the upper threshold can be assumed as non-uniform bright structures, such as vessels walls.

As another example, the upper and lower intensity thresholds can be defined locally, such as inside a sub-ROI like those described above. In these instances, the upper and lower intensity thresholds can be determined based on the max/min intensity of these sub-ROIs. For another non-limiting example, depth dependent upper and lower thresholds can be determined at each specific depth (e.g., $z_1$, $z_2$, and $z_3$) regarding statistics of the intensity values (e.g., maximum, minimum, median, mean) at the selected depth.

Figure 8:
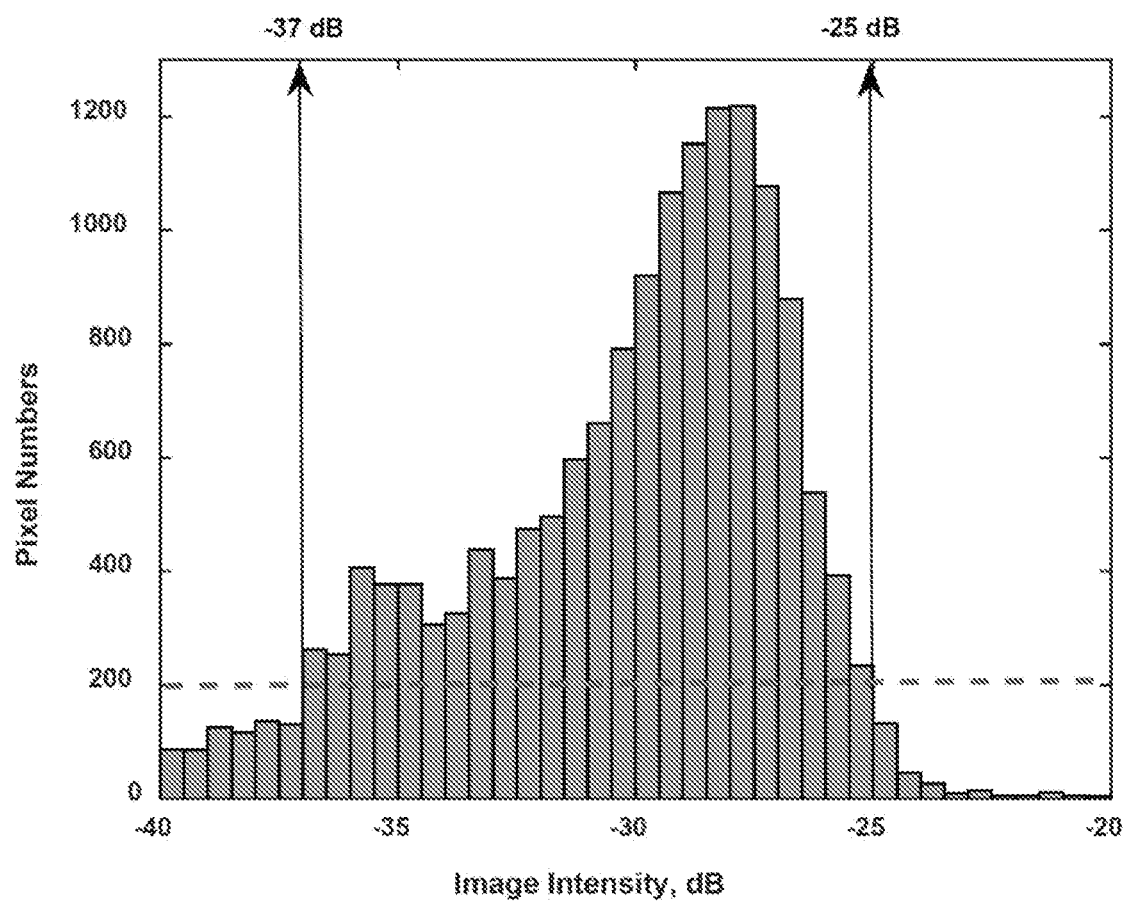
FIG. 8 shows an example of an image intensity histogram being used to determine intensity threshold values for detecting non-uniform structures.

As still another example, the upper and lower intensity thresholds can be determined based on an image pixel intensity histogram, such as the one shown in FIG. 8. For instance, the upper and lower thresholds can be determined at the two intensity boundaries where the pixel numbers drop to a certain level. In the example shown in FIG. 8, image intensities of −37 dB and −25 dB were selected as the lower and upper thresholds, respectively. The image intensities within the two boundaries have at least 200 pixels. Note that such histogram method could be implemented both globally (i.e., entire image or entire ROI) and locally (i.e., depth dependent or inside a sub-ROI).

Figure 9:
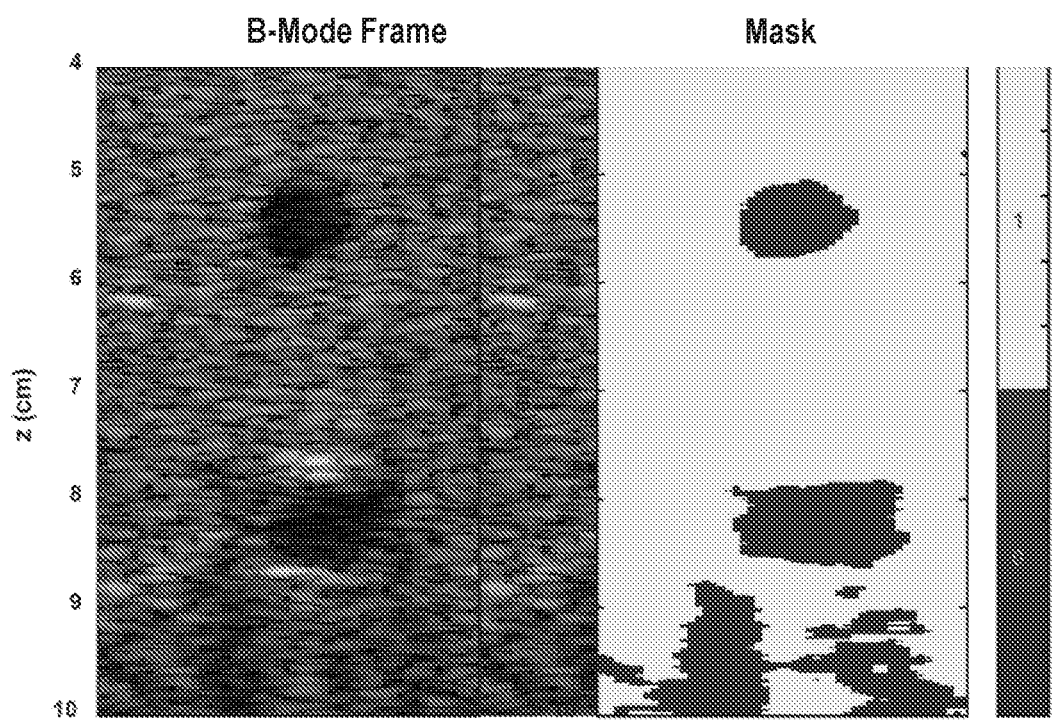
FIG. 9 shows an example of a B-mode image and a corresponding image mask based on detected non-uniform structures.

Once the image intensity thresholds are determined, a corresponding image mask can be calculated to mark out the non-uniform structures. FIG. 9 shows an example of an ROI selected from a liver B-mode image and the corresponding image mask with a lower threshold selected at 35 dB below the maximum intensity of the ROI. B-mode pixels with intensities within the thresholds are assigned mask values of "1", which represent relatively uniform structures; whereas pixels with intensities beyond the thresholds are assigned mask values of "0", which represent non-uniform structures such as vessels. Note that only a lower threshold was used in this example. An upper threshold can also be defined to mark out the bright interfaces such as vessel walls.

In most ACE methods, the selected ROI is divided into small data blocks along the axial direction (with or without overlap). The power spectra of all A-line segments in a given data block are calculated. The power spectra can then be averaged laterally across many A-line segments and the power ratio can be taken between two different frequencies (reference frequency method) or between the testing target and reference phantom (reference phantom method) to obtain the frequency power ratio at a certain depth. Note that the power ratio can also be calculated first and then averaged laterally to achieve the ratio value at that depth.

Figure 10:
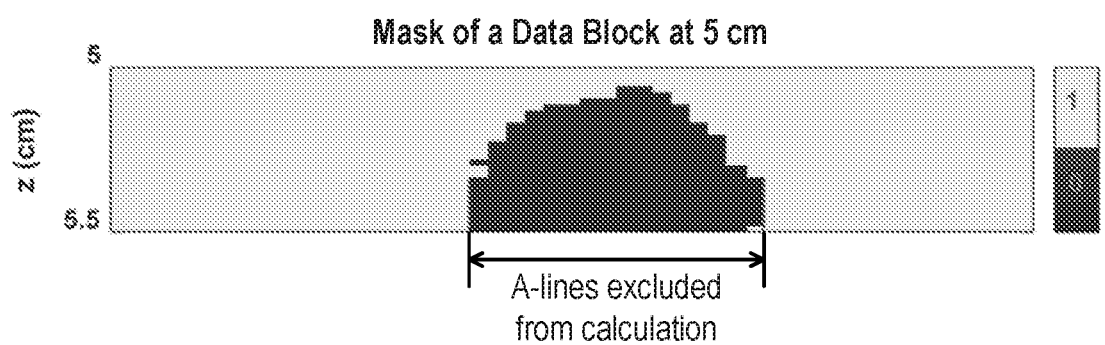
FIG. 10 shows an example of different non-uniform structure masks for different depths from FIG. 9.
Figure 10:
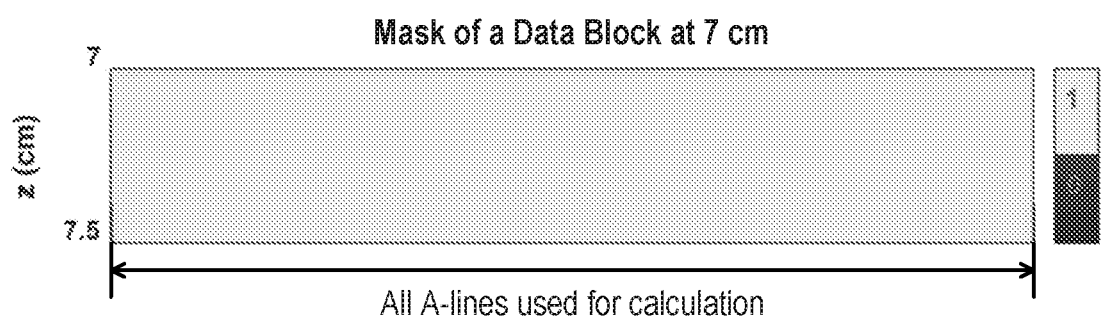

With the image mask calculated as introduced above, A-line segments with mask values of "0" (i.e., non-uniform structures) can be excluded from power spectra calculation and averaging. FIG. 10A shows a mask example of a 5-mm-long data block at around 5 cm depth. The double arrow labels the A-line segments excluded from the power spectra calculation. FIG. 10B shows another mask example of a data block at around 7 cm depth. All A-line segments can be used for calculation because the tissue structure is relatively uniform at this depth. This step can reduce the influence of non-uniform tissue structures on the frequency power ratio curves, facilitating more robust ACE performance.

Figure 11:
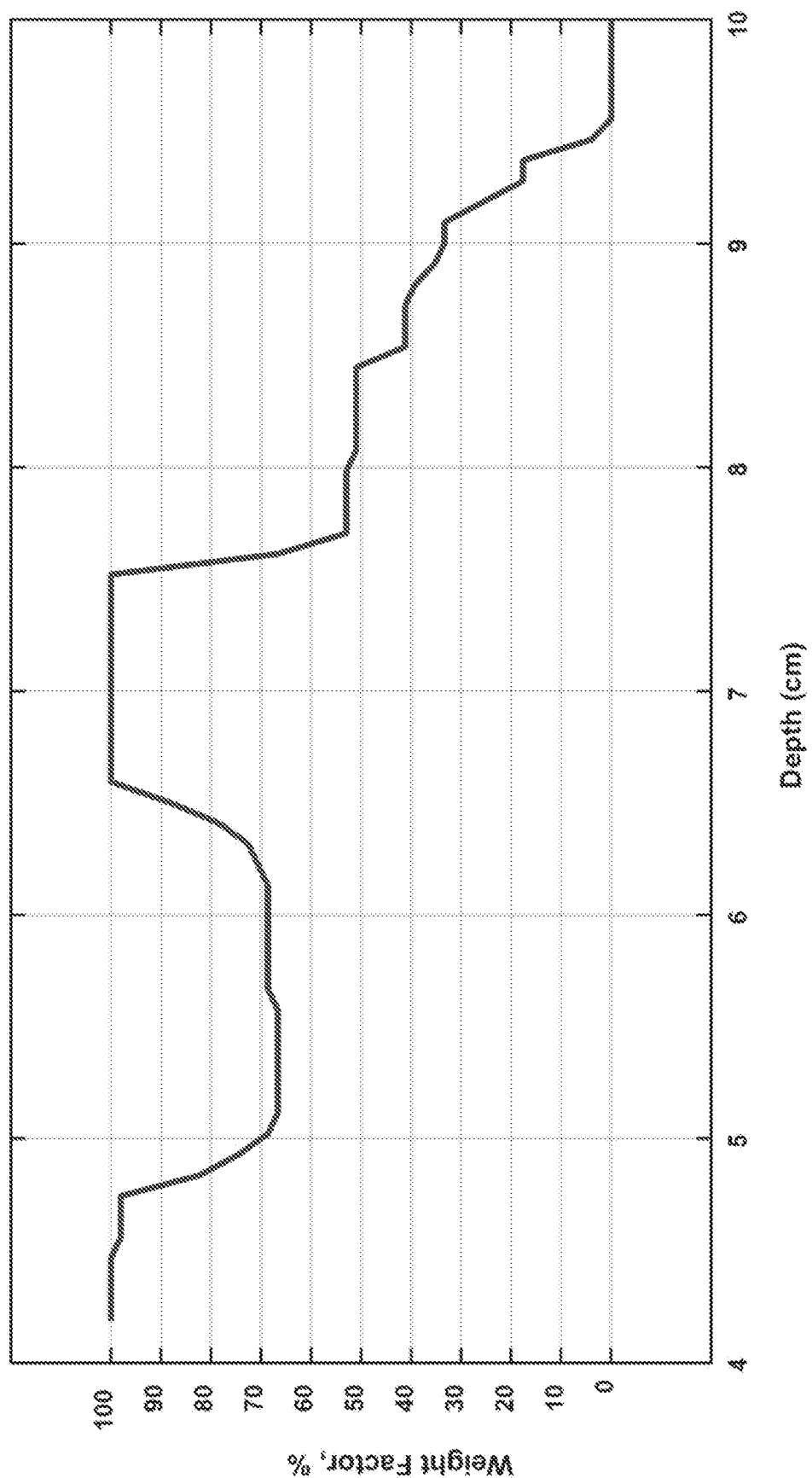
FIG. 11 shows an example plot of weighting factors as a function of depth for reducing contributions from non-uniform structures.

The more A-line segments used for averaging at a given depth, the more accurate the frequency power ratio value will be. Therefore, the number of A-line segments involved in calculation can be used as a weighting factor, when performing linear regression on the frequency power ratio curves across different depth ranges. One non-limiting example to obtain the weighting factor is to calculate the percentage of A-lines used for power spectra calculation as a fraction of total number of A-lines in a given data block. FIG. 11 shows an example of weighting factors as a function of depth calculated according to the image mask shown in FIG. 9. When the data block crosses non-uniform structures (e.g., the vessel at 5-6 cm), lower weights can be applied to the corresponding portion of frequency power ratio curves during linear regression. These weighting factors can also be used as a quality control. For example, the power ratio values with weights smaller than a predefined limit (e.g., 15%) can be eliminated from linear regression. In addition, a weighted linearity coefficient (e.g., $R^2$) can also be calculated with the weighting factors determined based on the percentage of A-lines used for power spectra calculation as a fraction of total number of A-lines in a given data block.

In one aspect, the systems and methods described in the present disclosure provide for improved ACE by detecting and removing non-uniform structures from a selected ROI before ACE analysis is implemented, where the non-uniform structures are identified based on the derivative of the frequency power ratio curve.

Figure 12A:
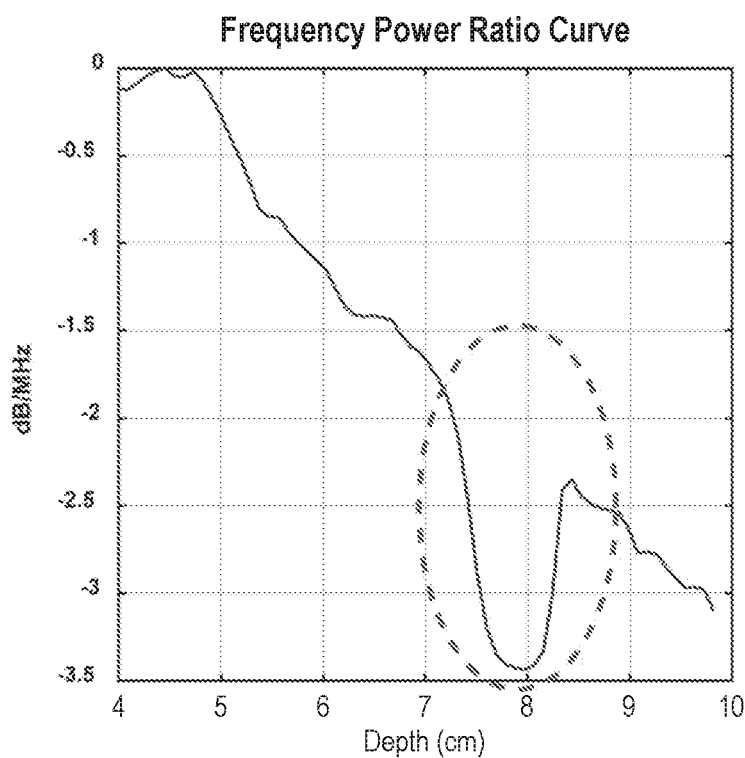
FIG. 12A shows an example frequency power ratio curve.
Figure 12B:
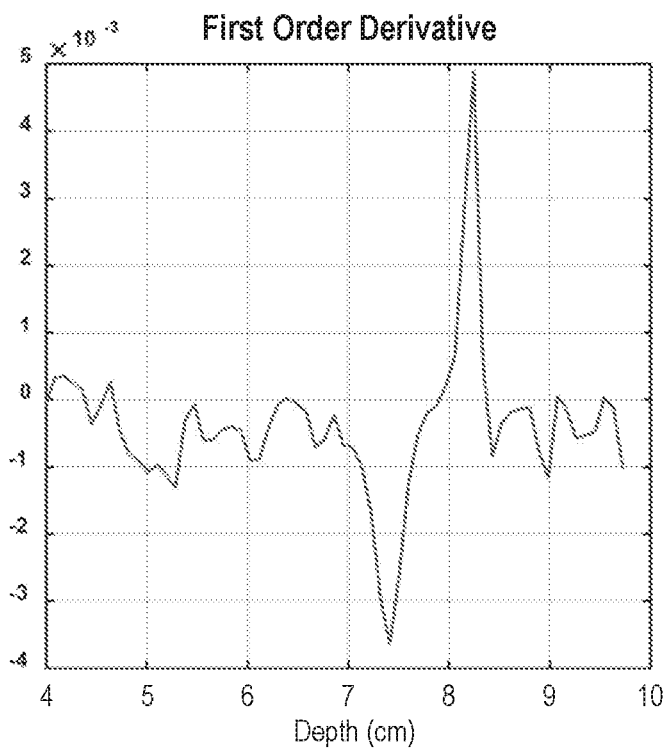
FIG. 12B shows the first order derivative of the frequency power ratio curve of FIG. 12A.

Non-uniform tissue structures sometimes create inflection points on the frequency power ratio curves. FIG. 12A shows an example of a frequency power ratio curve obtained from a liver ROI. The V-shaped discontinuity at around 8 cm (inside the red circle) is caused by the sudden change of the acoustic properties of the vessel wall (bright object) and vessel (dark object) as compared to surrounding tissues. These inflection points can be detected by calculating the derivative of the frequency power ratio curves, as shown in FIG. 12B. A derivative boundary can be set to eliminate the frequency power ratio values corresponding to the inflection points, or the portion in between from linear regression. Note that FIG. 12B shows an example of first order derivative. Higher order derivatives can also be used.

Figure 13:
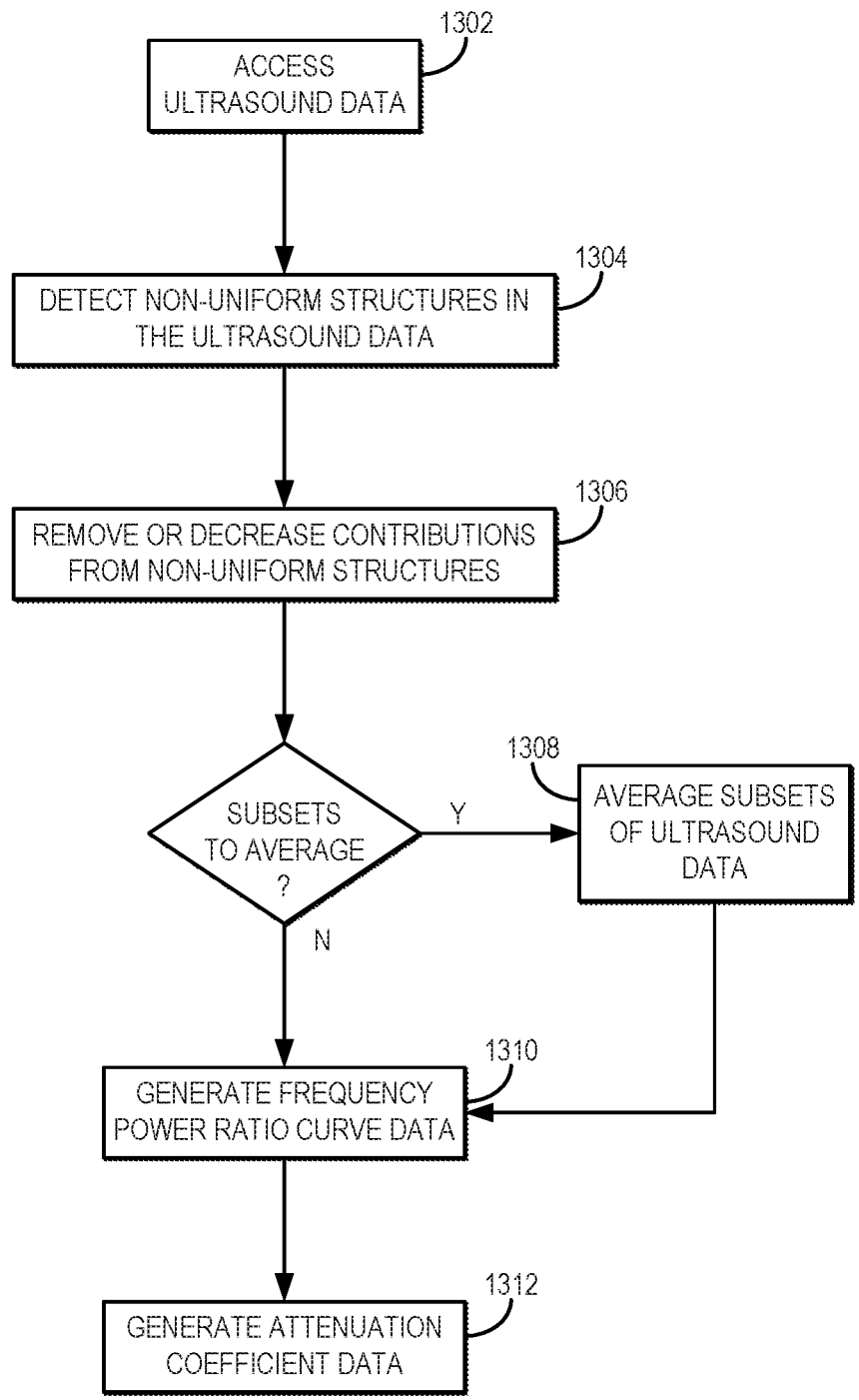
FIG. 13 is a flowchart setting forth the steps of a general workflow for improved ACE using embodiments described in the present disclosure.

Referring now to FIG. 13, a flowchart is illustrated as setting forth the steps of an example method for improving ACE using the techniques described in the present disclosure, which can be implemented separately or in combination.

The method includes accessing ultrasound data with a computer system, as indicated at step 1302. The ultrasound data can be accessed by retrieving previously acquired ultrasound data from a memory or other data storage device or medium. In other instances, the ultrasound data can be accessed by acquired such data with an ultrasound system and communicating, transmitting, or otherwise providing the acquired data to the computer system, which may be a part of the ultrasound system. For instance, the ultrasound data may be accessed in real-time as they are being acquired with the ultrasound system.

In some instances, when accessing the ultrasound data includes acquiring the ultrasound data, ultrasound jitters, or shifts, can be applied to the transmission channels, the receiver channels, or both, as described above. The ultrasound jitters can be applied to some or all of the available channels (transmission, receiver, or both), and can include random or non-random jitters.

Additionally or alternatively, when accessing the ultrasound data includes acquiring the ultrasound data in such a way so as to decrease correlations between A-lines. As one example, the ultrasound data can be acquired while the subject is freely breathing. As another example, the ultrasound data can be acquired while moving the ultrasound transducer probe so as to decrease the correlations between A-lines acquired from the same target region (e.g., by altering the ultrasound beam path). As another example, the ultrasound data can be acquired using sparsely sampled A-line acquisitions to enhance the frame rate. As still another example, the correlations of A-lines among different frames can be decreased by using different transmission sequences to acquire additional frames. For example, transmission sequences using plane/diverging waves, focused beams at different focusing depths, steered focused beams (i.e., crossbeam), or coded pulse excitations can be used in different transmission sequences to acquire different sets of ultrasound data.

Additionally or alternatively, when accessing the ultrasound data includes acquiring the ultrasound data, the ultrasound data can be acquired using transmission pulses with different characteristics (e.g., pulse length). For instance, the ultrasound data can be acquired over a plurality of different transmission events, with each transmission event implementing a different transmission pulse. As an example, the different transmission pulses can have different pulse lengths.

In some implementations, non-uniform structures can be identified in the ultrasound data, as indicated at step 1304. The non-uniform structures can then be removed or otherwise weighted so as not to contribute (or to reduce their contribution) to ACE, as indicated at step 1306. For instance, the contributions of non-uniform structures can be removed or otherwise decreased by generating a mask and applying that mask to the ultrasound data to remove the non-uniform structures. Alternatively, weight values can be generated and applied to reduce the contributions of non-uniform structures.

As one example, the non-uniform structures can be detected and their contributions removed or otherwise decreased based on intensity thresholding. For instance, a lower intensity threshold, an upper intensity threshold, or both, can be used to mask non-uniform structures in the ultrasound data. These threshold values can be determined globally (e.g., across a whole image, across a given ROI) or locally (e.g., across multiple different sub-ROIs, at different depth locations). The thresholds can be determined based on statistics of image intensity values (e.g., maximum intensity, minimum intensity, median intensity, mean intensity, image intensity histogram). Additionally or alternatively, the non-uniform structures can be detected and their contributions removed or otherwise decreased based on other vessel detection techniques, edge detection techniques, or other suitable techniques for identifying non-uniform structures. For example, other pixel-intensity based methods can be used for detecting non-uniform structures. As another example, machine learning or deep learning methods can also be used to identify non-uniform structures.

As described above, whether implemented separately or in combination, the acquired ultrasound data may include multiple different sets of ultrasound data having different properties or characteristics (e.g., acquired with different transmission channel jitter, acquired under different respiratory or cardiac motion, acquired under different probe motion, acquired with different A-line density, acquired with different pulse sequence, acquired with different transmission pulse). These different ultrasound data sets can be averaged as described above, and indicated at step 1308.

Frequency power ratio curve data are then generated from the averaged ultrasound data (or from the original ultrasound data when no averaging is performed), as indicated at step 1310. In some implementations, non-uniform structures can be detected and their contributions removed or otherwise decreased based on a derivative of the frequency power ratio curve data. For instance, first or higher order derivatives of the frequency power ratio curve data can be used to identify inflection points corresponding to non-uniform structures, such as vessel walls and vessels. The frequency power ratio curve data can be generated for an ROI, or for sub-ROIs contained within a selected ROI. The frequency power ratio curve data can be generated using a reference phantom technique, a reference frequency technique, or other suitable technique.

Attenuation coefficient data are then generated from the frequency power ratio curve data, as indicated at step 1312. When the frequency power ratio curve data contain frequency power ratio curves computed in multiple different sub-ROIs, different attenuation coefficient data can be estimated for each sub-ROI and combined or otherwise used to generate the final attenuation coefficient data. As one example, a linearity metric, such as an $R^2$ metric, corresponding to each sub-ROI can be used as a quality control metric for determining the final attenuation coefficient data. For instance, the attenuation coefficient data from the sub-ROI having the maximum linearity metric value can be assigned as the final attenuation coefficient data for the entire ROI. Alternatively, the median value or the mean value of the attenuation coefficient data across the sub-ROIs can be assigned as the final attenuation coefficient data.

Figure 14:
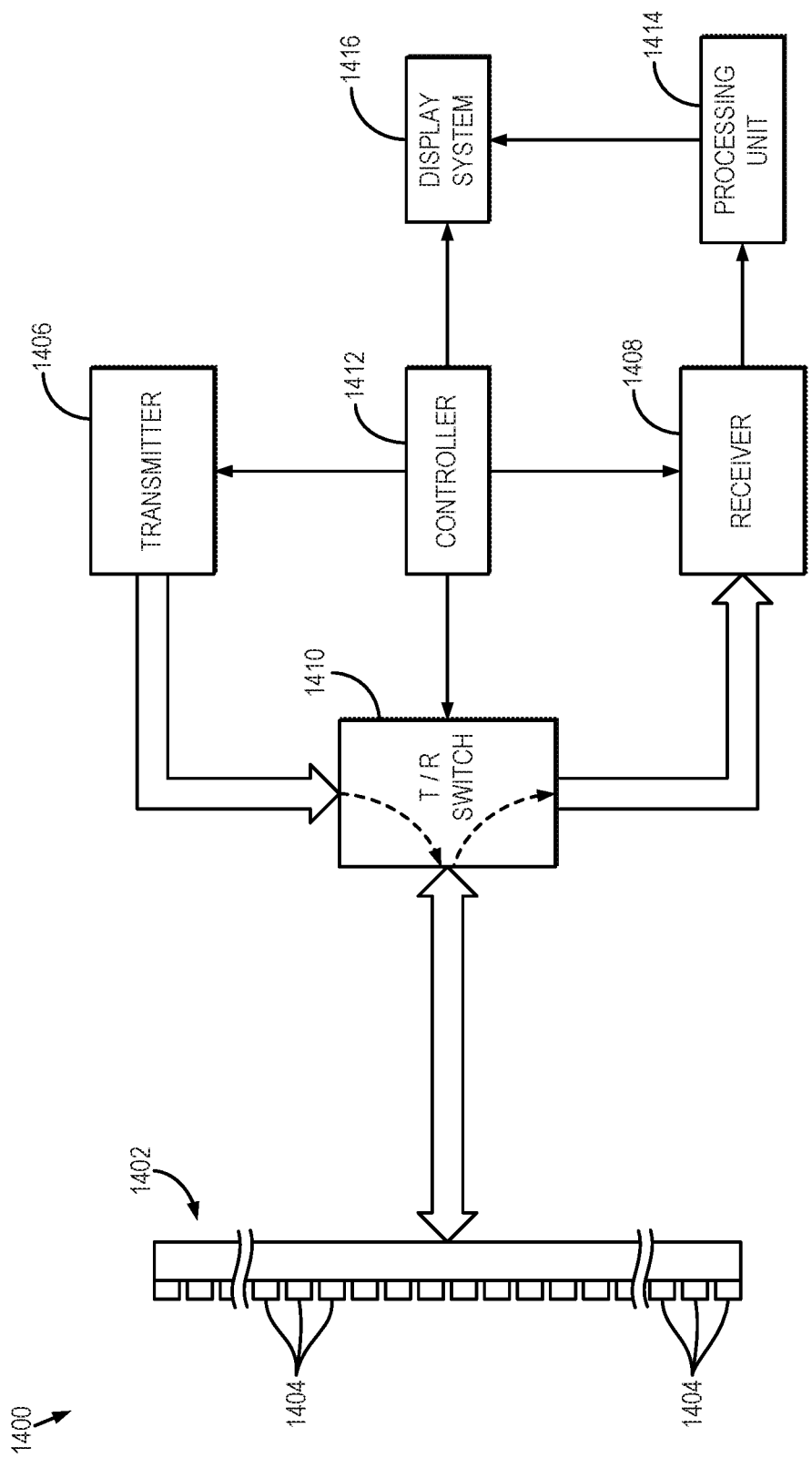
FIG. 14 is a block diagram of an example ultrasound system that can implement the methods described in the present disclosure.

FIG. 14 illustrates an example of an ultrasound system 1400 that can implement the methods described in the present disclosure. The ultrasound system 1400 includes a transducer array 1402 that includes a plurality of separately driven transducer elements 1404. The transducer array 1402 can include any suitable ultrasound transducer array, including linear arrays, curved arrays, phased arrays, and so on. Similarly, the transducer array 1402 can include a 1D transducer, a 1.5D transducer, a 1.75D transducer, a 2D transducer, a 3D transducer, and so on.

When energized by a transmitter 1406, a given transducer element 1404 produces a burst of ultrasonic energy. The ultrasonic energy reflected back to the transducer array 1402 (e.g., an echo) from the object or subject under study is converted to an electrical signal (e.g., an echo signal) by each transducer element 1404 and can be applied separately to a receiver 1408 through a set of switches 1410. The transmitter 1406, receiver 1408, and switches 1410 are operated under the control of a controller 1412, which may include one or more processors. As one example, the controller 1412 can include a computer system.

The transmitter 1406 can be programmed to transmit unfocused or focused ultrasound waves. In some configurations, the transmitter 1406 can also be programmed to transmit diverged waves, spherical waves, cylindrical waves, plane waves, or combinations thereof. Furthermore, the transmitter 1406 can be programmed to transmit spatially or temporally encoded pulses.

The receiver 1408 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 1406 and the receiver 1408 can be programmed to implement a high frame rate. For instance, a frame rate associated with an acquisition pulse repetition frequency ("PRF") of at least 100 Hz can be implemented. In some configurations, the ultrasound system 1400 can sample and store at least one hundred ensembles of echo signals in the temporal direction.

The controller 1412 can be programmed to design an acquisition sequence using the techniques described in the present disclosure, or as otherwise known in the art. In some embodiments, the controller 1412 receives user inputs defining various factors used in the design of the acquisition sequence. In some examples, ultrasound data can be acquired using a plane wave ultrasound acquisition. In other examples, ultrasound data can be acquired using an acquisition scheme that implements one or more focused ultrasound beams. Still other examples for acquiring ultrasound data can be used according to the knowledge of those skilled in the art.

A scan can be performed by setting the switches 1410 to their transmit position, thereby directing the transmitter 1406 to be turned on momentarily to energize transducer elements 1404 during a single transmission event according to the designed acquisition sequence. The switches 1410 can then be set to their receive position and the subsequent echo signals produced by the transducer elements 1404 in response to one or more detected echoes are measured and applied to the receiver 1408. The separate echo signals from the transducer elements 1404 can be combined in the receiver 1408 to produce a single echo signal.

The echo signals are communicated to a processing unit 1414, which may be implemented by a hardware processor and memory, to process echo signals or images generated from echo signals. As an example, the processing unit 1414 can acquire ultrasound data using acquisition parameters (e.g., frequency bandwidth and depth) that are determined using the methods described in the present disclosure. As another example, the processing unit 1414 can estimate attenuation coefficient values and generate attenuation coefficient maps from data acquired using the methods described in the present disclosure.

Figure 15:
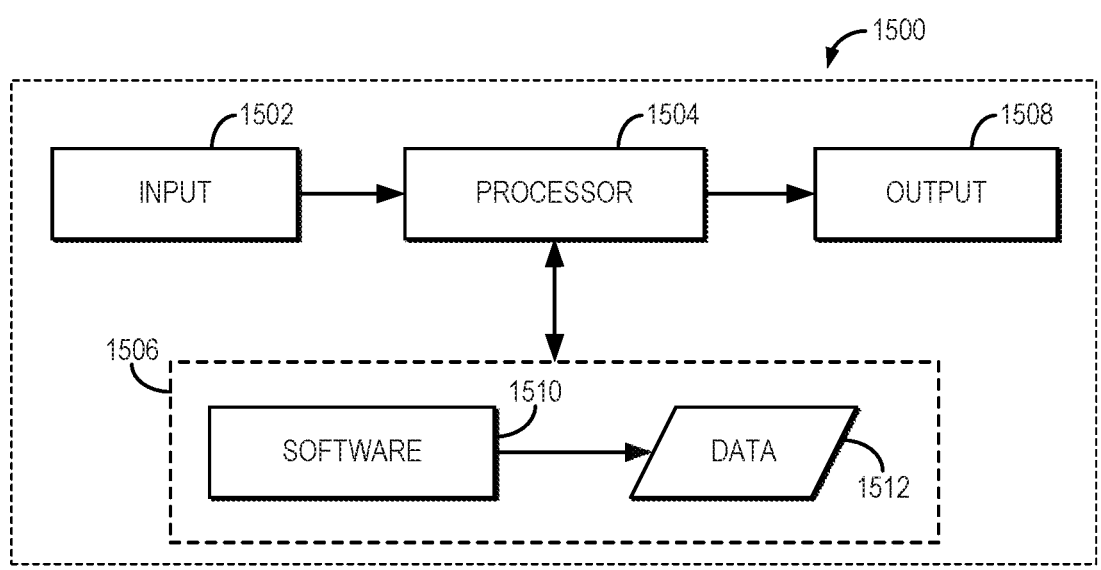
FIG. 15 is a block diagram of an example computer system that can implement the methods described in the present disclosure.

Referring now to FIG. 15, a block diagram of an example of a computer system 1500 that can perform the methods described in the present disclosure is shown. The computer system 1500 generally includes an input 1502, at least one hardware processor 1504, a memory 1506, and an output 1508. Thus, the computer system 1500 is generally implemented with a hardware processor 1504 and a memory 1506.

In some embodiments, the computer system 1500 can be a workstation, a notebook computer, a tablet device, a mobile device, a multimedia device, a network server, a mainframe, one or more controllers, one or more microcontrollers, or any other general-purpose or application-specific computing device.

The computer system 1500 may operate autonomously or semi-autonomously, or may read executable software instructions from the memory 1506 or a computer-readable medium (e.g., a hard drive, a CD-ROM, flash memory), or may receive instructions via the input 1502 from a user, or any another source logically connected to a computer or device, such as another networked computer or server. Thus, in some embodiments, the computer system 1500 can also include any suitable device for reading computer-readable storage media.

In general, the computer system 1500 is programmed or otherwise configured to implement the methods and algorithms described in the present disclosure. For instance, the computer system 1500 can be programmed to generate attenuation coefficient data from ultrasound data.

The input 1502 may take any suitable shape or form, as desired, for operation of the computer system 1500, including the ability for selecting, entering, or otherwise specifying parameters consistent with performing tasks, processing data, or operating the computer system 1500. In some aspects, the input 1502 may be configured to receive data, such as data acquired with an ultrasound system. Such data may be processed as described above to generate attenuation coefficient data. In addition, the input 1502 may also be configured to receive any other data or information considered useful for generating attenuation coefficient data using the methods described above.

Among the processing tasks for operating the computer system 1500, the one or more hardware processors 1504 may also be configured to carry out any number of post-processing steps on data received by way of the input 1502.

The memory 1506 may contain software 1510 and data 1512, such as data acquired with an ultrasound system, and may be configured for storage and retrieval of processed information, instructions, and data to be processed by the one or more hardware processors 1504. In some aspects, the software 1510 may contain instructions directed to generating attenuation coefficient data according to embodiments described in the present disclosure.

In addition, the output 1508 may take any shape or form, as desired, and may be configured for displaying ultrasound images, attenuation coefficient maps, other mechanical property maps generated from the ultrasound data and/or attenuation coefficient maps, in addition to other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed:

1. A method for estimating ultrasound attenuation coefficient data using an ultrasound system, the method comprising:
   (a) accessing with a computer system, ultrasound data acquired from a subject with an ultrasound system, wherein the ultrasound data contain subsets of ultrasound data acquired with different characteristics, wherein the different characteristics result in changes in signal interference patterns between the subsets of ultrasound data;
   (b) generating averaged ultrasound data with the computer system by averaging the ultrasound data corresponding to the subsets of ultrasound data;
   (c) generating frequency power ratio curve data from the averaged ultrasound data using the computer system, wherein the frequency power ratio curve data have reduced frequency power ratio curve oscillations, wherein the frequency power ratio curve oscillations are reduced based on averaging the subsets of ultrasound data acquired with the different characteristics that cause changes in signal interference patterns between the subsets of ultrasound data; and
   (d) generating attenuation coefficient data from the frequency power ratio curve data using the computer system.

2. The method as recited in claim 1, wherein the subsets of ultrasound data correspond to ultrasound data acquired by applying jitters to one or more channels of the ultrasound system.

3. The method as recited in claim 2, wherein the jitters are applied to one or more transmission channels of the ultrasound system.

4. The method as recited in claim 2, wherein the jitters are applied to one or more receiver channels of the ultrasound system.

5. The method as recited in claim 2, wherein the jitters are applied to both one or more transmission channels of the ultrasound system and one or more receiver channels of the ultrasound system.

6. The method as recited in claim 2, wherein the jitters are randomly assigned jitters.

7. The method as recited in claim 1, wherein the subsets of ultrasound data correspond to ultrasound data acquired while the subject was freely breathing, such that different subsets of the ultrasound data are acquired under different respiratory motion conditions.

8. The method as recited in claim 1, wherein the subsets of ultrasound data correspond to ultrasound data acquired while an ultrasound transducer was moved over a target region in the subject, such that different subsets of the ultrasound data are acquired under different transducer motion conditions.

9. The method as recited in claim 1, wherein the subsets of ultrasound data correspond to ultrasound data acquired using different A-line densities.

10. The method as recited in claim 1, wherein the subsets of ultrasound data correspond to ultrasound data acquired using transmission pulses having different characteristics.

11. The method as recited in claim 10, wherein the different characteristics are different pulse lengths.

12. The method as recited in claim 1, wherein the subsets of ultrasound data correspond to ultrasound data acquired by using different pulse sequence designs.

13. The method as recited in claim 12, wherein the different pulse sequence designs include two or more of plane waves, diverging waves, focused beams at different focusing depths, steered focused beams, and coded pulse excitations.

14. The method as recited in claim 1, wherein the attenuation coefficient data comprise an attenuation coefficient map that visually depicts a spatial distribution of attenuation coefficient values in a region from which the ultrasound data were acquired.

* * * * *